United States Patent [19]

Hood et al.

[11] 4,252,769

[45] Feb. 24, 1981

[54] APPARATUS FOR THE PERFORMANCE OF CHEMICAL PROCESSES

[75] Inventors: Leroy E. Hood, Altadena; Michael W. Hunkapiller, San Gabriel, both of Calif.

[73] Assignee: California Institute of Technology, Pasadena, Calif.

[21] Appl. No.: 106,828

[22] Filed: Dec. 26, 1979

[51] Int. Cl.³ .......................... G01N 1/18; G01N 9/30
[52] U.S. Cl. ...................................... 422/50; 422/68; 422/81; 260/112.5 R
[58] Field of Search .................... 422/68, 50, 64, 81; 23/230 B; 260/112.5 R; 137/103, 526

[56] References Cited

U.S. PATENT DOCUMENTS

| | | | |
|---|---|---|---|
| 3,717,436 | 2/1973 | Penhasi et al. | 260/112.5 R |
| 3,725,010 | 4/1973 | Penhasi | 422/64 |
| 3,986,521 | 10/1976 | Wittman-Liebold et al. | 137/334 |

OTHER PUBLICATIONS

Edman et al., "A Protein Sequenator," European J. of Biochem., 1967, pp. 80–91.
Whittman-Liebold, "Amino Acid Sequence Studies of Ten Ribosomal Protein of *Escheichia Coli* with . . . Improved Sequenator . . .", Hoppe-Seyler's Z. Physiol. Chem. 354, 1415 (1973).
Analytical Biochemistry, 75, 621 (1976).
Hunkapiller et al., "Direct Microsequence Analysis of Polypeptides Using an Improved Sequenator . . . ," Biochemistry 2124 (1978).

*Primary Examiner*—Ronald Serwin
*Attorney, Agent, or Firm*—Joseph E. Mueth

[57] ABSTRACT

An improved apparatus for the performance of chemical processes having a reaction chamber with an open end, a reaction cell mounted within the chamber and having a substantially cylindrical interior wall in which is formed an annular groove, and means for spinning the cell about its axis to distribute a chemical compound on the interior wall as a thin film, which includes a closure member mounted for rotation about an axis displaced from the axis of the cell, and a fluid conduit extending through the closure member and terminating at an inner end within the cell for the withdrawal of fluid therefrom. The inner end of the conduit is displaced from the axis of rotation of the closure member and is positioned substantially opposite the annular groove such that it is actuable for adjustment between a first location displaced radially from the annular groove and a second location substantially within the groove by rotation of the closure member through a preselected angle.

17 Claims, 14 Drawing Figures

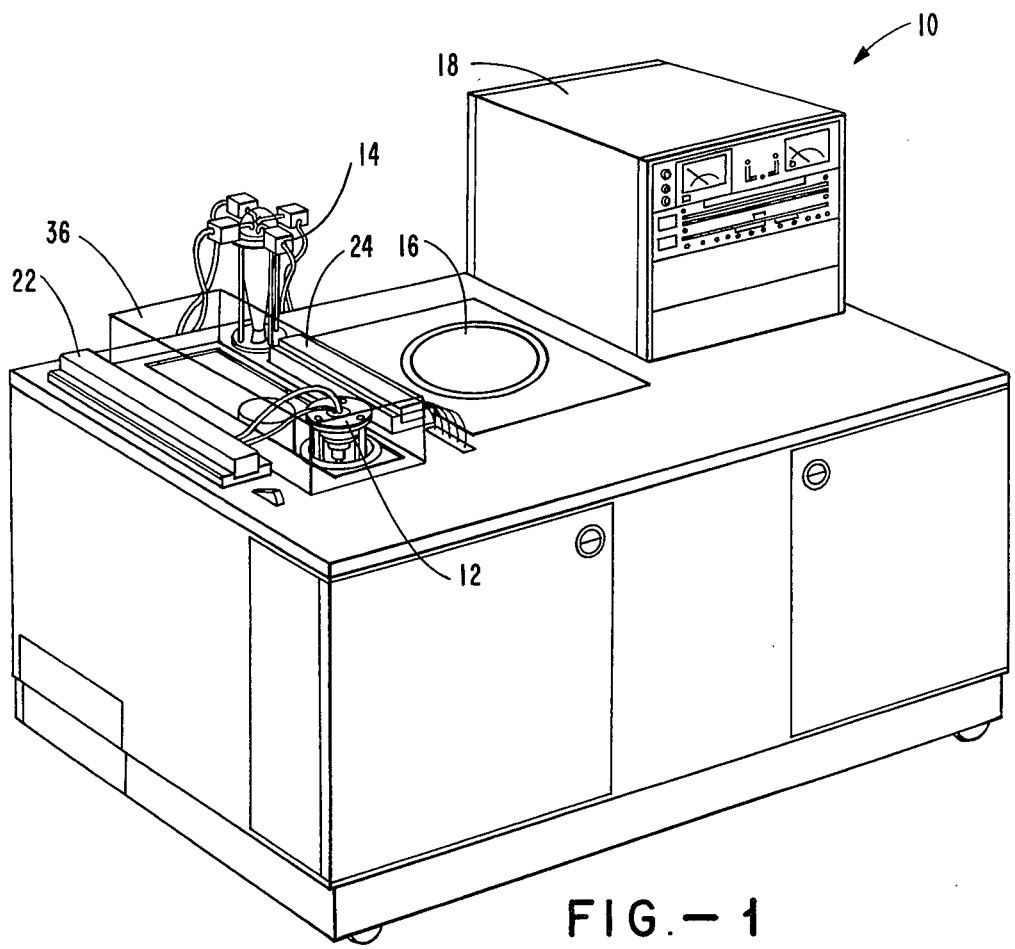
FIG.—1
FIG.—2
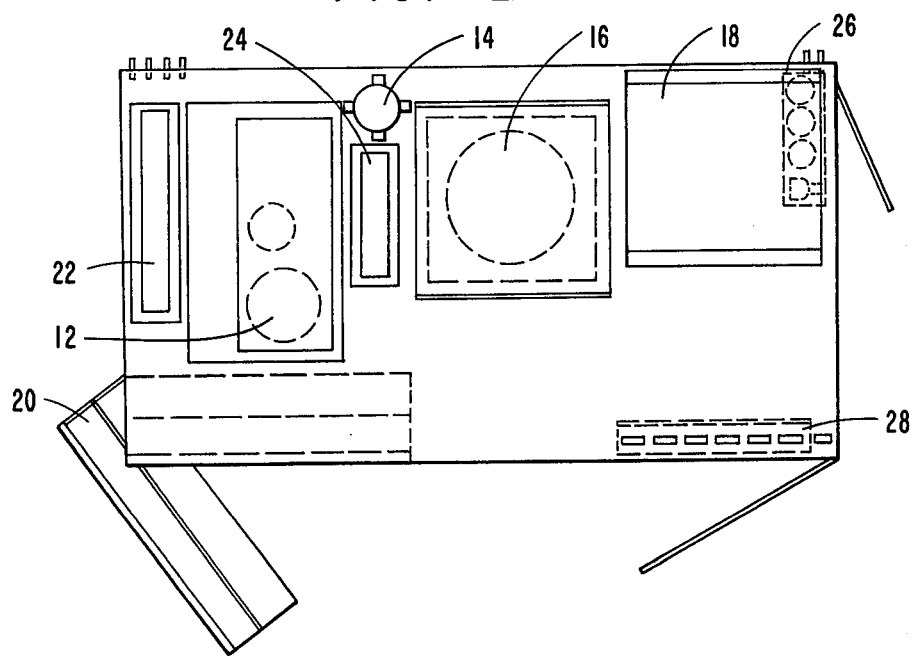

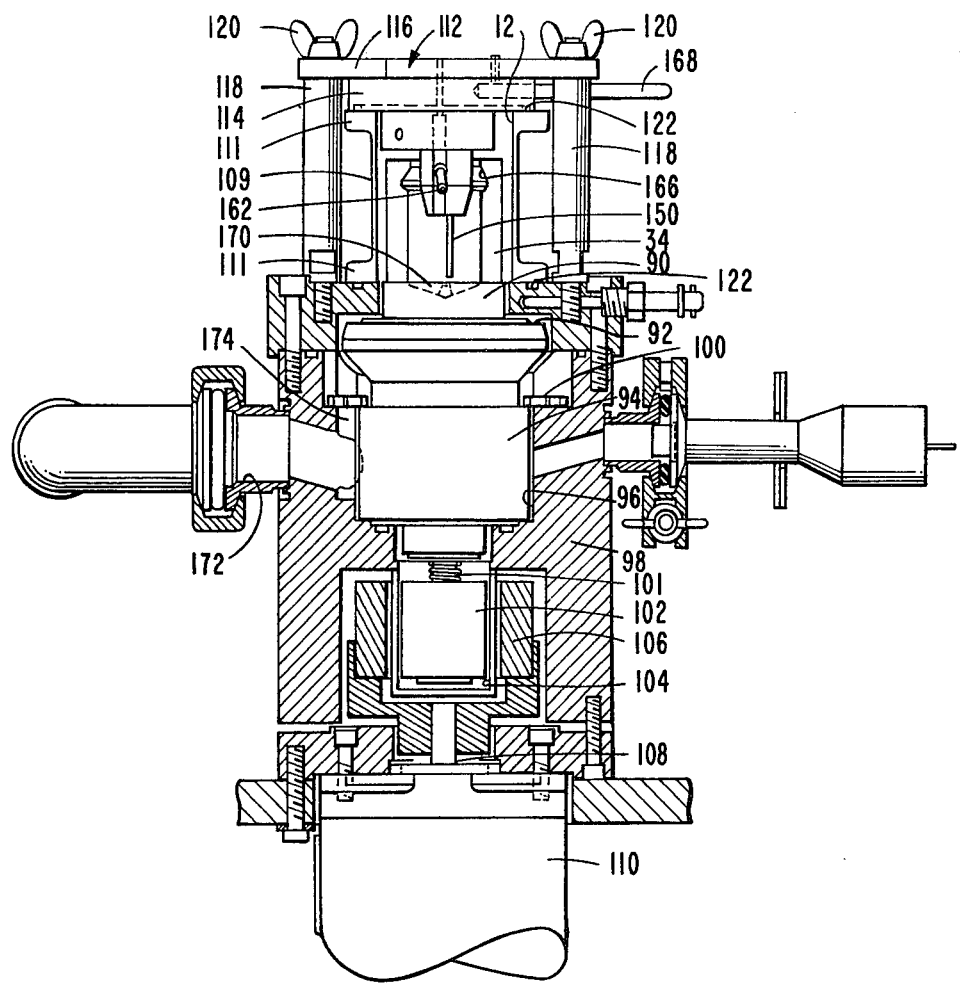
FIG.—4
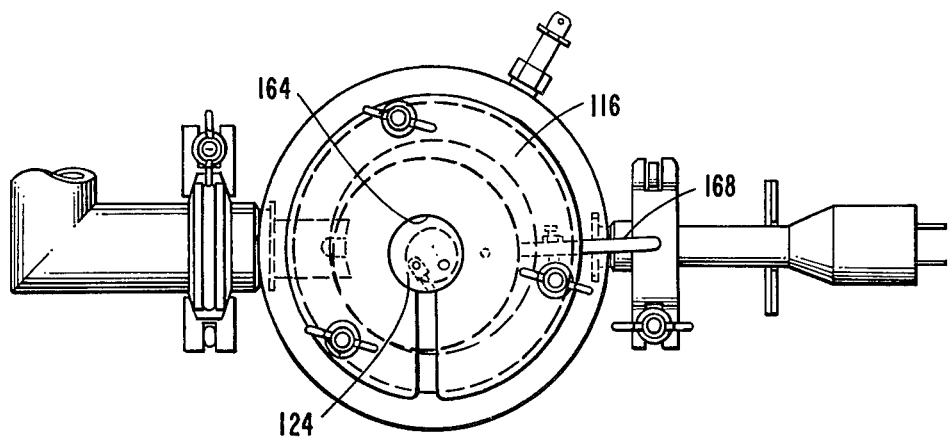
FIG.—5

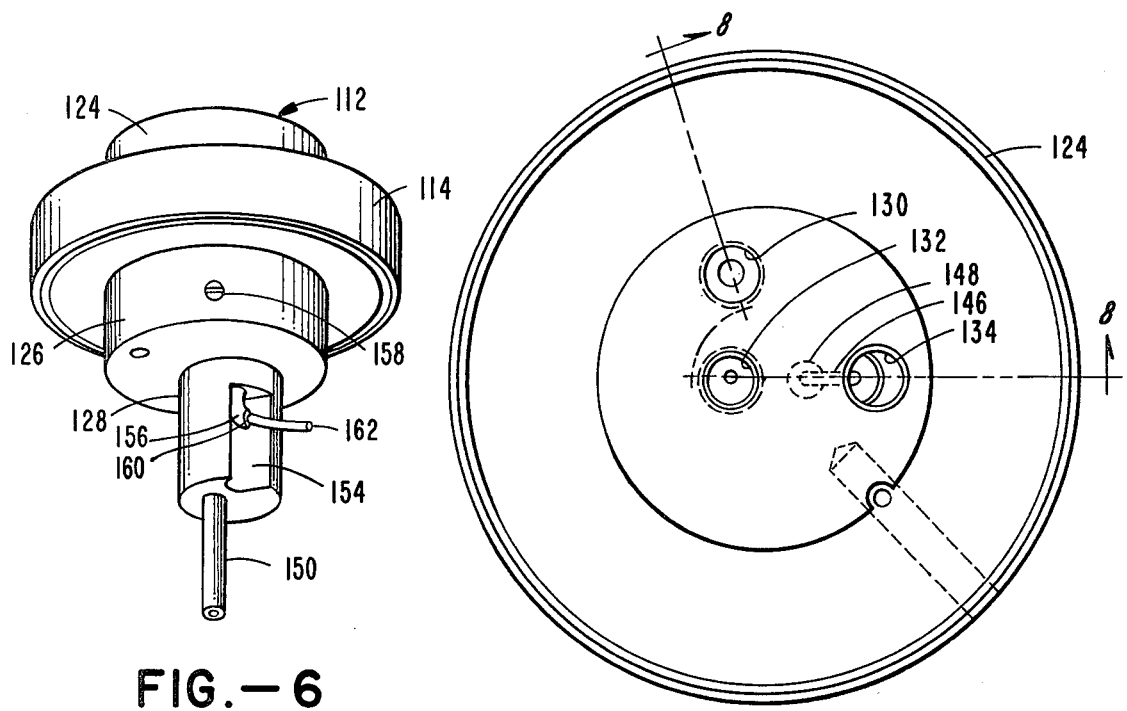
FIG.-6
FIG.-7
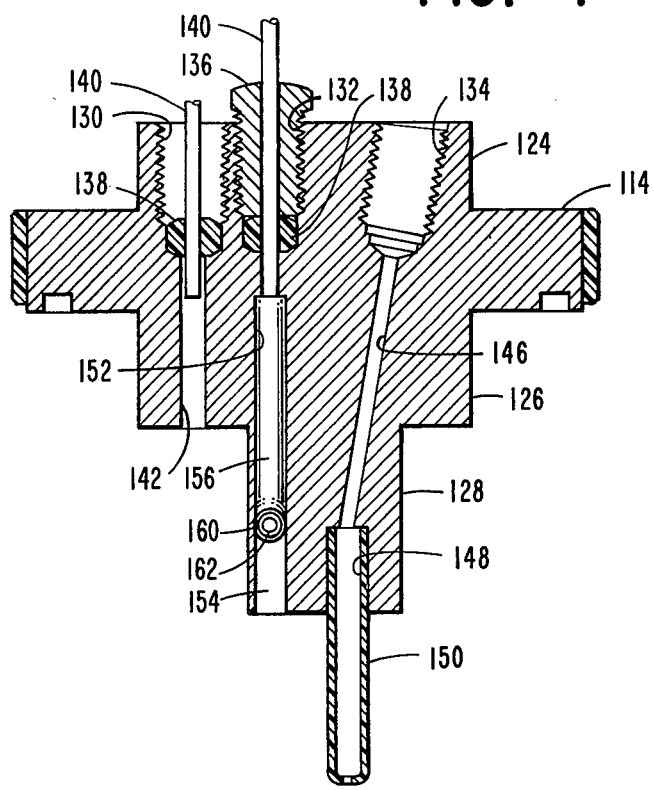
FIG.-8

APPARATUS FOR THE PERFORMANCE OF CHEMICAL PROCESSES

BACKGROUND OF THE INVENTION

This invention relates generally to an improved apparatus for the performance of chemical processes and, more particularly, to an improved apparatus for automatically performing the sequential degradation of protein or peptide chains containing a large number of amino acid units for purposes of determining the sequence of those units.

The linear sequence of the amino acid units in proteins and peptides is of considerable interest as an aid to understanding their biological functions and ultimately synthesizing compounds performing the same functions. Although a variety of techniques have been used to determine the linear order of amino acids, probably the most successful is known as the Edman Process. Various forms of the Edman Process and apparatuses for automatically performing the processes are described in the following publications:

Edman and Begg, "A protein Sequenator," European J. Biochem. 1 (1967) 80-91; Wittman-Liebold, "Amino Acid Sequence Studies of Ten Ribosomal Proteins of *Escherichia coli* with an Improved Sequenator Equipped with an Automatic Conversion Device," Hoppe-Seyler's Z. Physiol. Chem. 354, 1415 (1973); Wittmann-Liebold et al., "A Device Coupled to a Modified Sequenator for the Automated Conversion of Anilino-thiazolinones into PTH Amino Acids," Analytical Biochemistry 75, 621 (1976); Hunkapiller and Hood, "Direct Microsequence Analysis of Polypeptides Using an Improved Sequenator, A Nonprotein Carrier (Polybrene), and High Pressure Liquid Chromatography," Biochemistry 2124 (1978); U.S. Pat. No. 3,725,010 issued to Penhasi on Apr. 3, 1973, for "Apparatus for Automatically Performing Chemical Processes;" and U.S. Pat. No. 3,717,436 issued to Penhasi et al. on Feb. 20, 1973, for "Process for the Sequential Degradation of Peptide Chains." Briefly, as discussed in the above publications, the Edman sequential degradation processes involve three stages: coupling, cleavage, and conversion. In the coupling stage phenyl isothiocyanate reacts with the N-terminal $\alpha$ amino group of the peptide to form the phenylthiocarbamyl deriviative. In the cleavage step anhydrous acid is used to cleave the phenylthiocarbamyl derivative, i.e., the anilinothiazolinone. After extraction of the thiazolinone the residual peptide is ready for the next cycle of coupling and cleavage reactions. Aqueous acid is used to convert the thiazolinone to the phenylthiohydantoin which may be analyzed in an appropriate manner such as by chromatography.

The automated apparatus of the Penhasi U.S. Pat. No. 3,725,010 patent, as modified in the above-referenced articles of Wittmann-Liebold and the article of Hunkapiller and Hood, is the most sophisticated prior sequenator known to us. The reactions in this sequenator are carried on in a thin film formed on the inside wall of a rotating reaction cell located within a closed reaction chamber. Means are provided for introducing and removing liquids and gases relative to the chamber, and the reaction cell is substantially closed off from the reaction chamber such that liquids in the reaction cell are substantially trapped therein but gases fed into the reaction chamber may enter and circulate in the reaction cell. The protein or peptide being analyzed is initially placed in the rotating reaction cell, followed by the sequential introduction and withdrawal of the various reagents and solvents necessary for carrying out the coupling and cleavage reactions. Upon completion of the cleavage step, the resulting thiazolinone is extracted and transferred either to a separate flask for conducting the conversion step or to an apparatus for collection and drying of the various fractions. In cases where the conversion process is not performed immediately in a conversion flask, the process may be performed later on a number of fractions simultaneously.

The introduction and withdrawal of fluids relative to the reaction cell has generally been achieved with fluid conduits passing through a plug which seals an opening in the upper wall of the reaction chamber and depends therefrom to a location within the reaction cell. Fluids are introduced directly into the reaction cell at a point adjacent the bottom thereof, and are withdrawn from an annular groove in the cylindrical interior surface of the reaction cell. The fluid to be withdrawn is forced into the annular groove by centrifugal force when the cup is rotated at a high rate, and is withdrawn through a conduit having an inner end projecting into the groove. This effluent conduit thus acts as a scoop for removing the reaction products and by-products and the extracting solvents from the reaction cell. Because the orientation of the inner end of the effluent line relative to the groove and the reaction cell is critical to the performance of the scooping operation, the effluent lines have been constructed to be externally adjustable in extension and angular orientation relative to the plug. The degradable elastomers and other materials associated with such adjustable fittings have caused contamination of the sample, both through reaction with the chemicals in the system and the production of leaks to the atmosphere.

Drying of the various reagents and solvents at the appropriate times is produced in part by vacuum means. It is generally desirable to vacuum dry the sample in two steps to avoid disruption of the system by boiling the more volatile components. A restricted vacuum is thus first applied to the system to draw out the bulk of the volatile components. The full output of the vacuum pump is then applied to complete the drying operation. Restriction of the vacuum is accomplished through use of a connecting passage having a much more restricted bore than the passage used to achieve full vacuum. The passages are opened and closed by respective solenoid valves kept at room temperature. In this configuration, semivolatile reagents and solvents have a tendency to condense on the bore of the restricted vacuum tube and also within the bodies of the two vacuum valves. It is thus very difficult to fully evacuate the reagents and solvents from these areas at the desired times, contaminating the chemistry of subsequent coupling and cleavage steps.

The prior devices have each used a number of degradable elastomeric seals which can contaminate the system both by leakage and reaction with its components.

The contamination caused by the several features described above has a cumulative effect over the duration of a sequential degradation process. The sample and the reagents within the reaction cell thus become more and more contaminated, hindering the desired coupling and cleavage reactions and causing a number of undesired reactions to take place. The yield from each complete cycle of the apparatus is thus decreased and a series of contaminants are introduced into the fractions.

While these effects may be overlooked in some cases where large amounts of the protein or peptide sample are available or where the chain has a relatively small number of units, they become devastating in cases where the chain has a very large number of units or only very small amounts of the particular protein or peptide are available. Both of these circumstances are present in the case of interferon, a small protein made in human cells in response to certain viral infections. Interferon has recently caused a great deal of excitement in the world of clinical medicine because it promises to be an effective agent for arresting viral infections and it appears to offer considerable hope as an anti-cancer reagent. Interferon is produced and, accordingly, is available only in very small quantities. Currently, virtually the entire world's production of the two types of human interferon originates in the relatively few world centers that have access to large quantities of human white blood cells (leukocyte interferon) or certain human cells in tissue culture (fibroblast interferon). Because of this limited productive capacity for interferon, it has been difficult to carry out well controlled clinical studies and fundamental analyses of how this molecule functions. To further complicate the picture, interferon is composed of a chain of approximately 150 amino acid residues, which must be individually cleaved from the chain for analysis. The contamination losses inherent in the operation of the prior sequenators have thus far prevented the sequencing of any but the first few amino acid units of interferon with the very small available quantities of the protein. Beyond the first few cleavage cycles, the small sample becomes contaminated to the point at which positive results are unobtainable.

Therefore, in many applications, it is desirable to provide an apparatus for performing chemical processes such as the sequencing of interferon which maintains the sample and everything coming in contact with the sample as free of contamination as possible to enable the maximum number of sequencing cycles to be successfully performed with the minimum amount of sample.

SUMMARY OF THE INVENTION

Briefly, the present invention comprises an improved apparatus for the performance of chemical processes of the type including a base, a vessel on the base at least partially defining a reaction chamber having an open end, a reaction cell mounted within the chamber and having a substantially cylindrical axially directed interior wall in which is formed an annular groove, and means for spinning the cell about its access to distribute a chemical compound on the interior wall as a thin film, wherein the improvement comprises a closure member mounted for rotation between a plurality of positions relative to the base about an axis displaced a first predetermined distance from the axis of the cell, the closure member sealingly engaging the open end of the chamber for each of the positions; and a first fluid conduit extending through the closure member and terminating at an inner end within the cell for the withdrawal of fluid therefrom, the interior end being displaced a second predetermined distance from the axis of rotation of the closure member at a location substantially opposite the annular groove; such that the inner end of the first conduit is actuable for purposes of adjustment between a first location displaced radially from the inner groove and a second location substantially within the groove by rotation of the closure member through a preselected angle, the first conduit being operable to receive fluid from the groove for the inner end in the second location.

The apparatus may include a second fluid conduit carried by the closure member and terminating at an inner end within the cell for the introduction of fluids into the cell, the second conduit actuable between third and fourth locations spaced from the axis of the cell by rotation of the closure member through a preselected angle. The first conduit may be a flexible tube received within a curved rigid conduit adjacent the underside of the closure member for directing the inner end of the flexible tube generally away from the axis of rotation of the closure member to form an acute angle with the radius of the reaction cell. The first and second conduits may be fixedly anchored into the closure member in sealing relationship therewith by resilient ferrules engaged with the exterior of the first and second conduits in a force fit relationship and compressed by screw thread means to form a stationary seal between the exterior of the conduits and the closure member. The conduits and the resilient ferrules are both preferably made of a fluorocarbon polymer or other material which is substantially chemically inert.

The apparatus may be provided with a vacuum source connectable to the chamber through first and second valve means in series with each other. The first valve means is actuable between a fully open and a fully closed condition while the second valve means is actuable between a fully open condition and a restricted open condition. Full vacuum is thus applied to the chamber when both valve means are in the fully open condition, and a restricted vacuum is applied when the first valve means is in the fully open condition and the second valve means is in the restricted open condition. No vacuum is applied when the first valve means is in the fully closed condition. The second valve means is located between the first valve means and the vacuum source. Both the first and second valve means and the lines connecting the valves to each other and to the chamber may be located within a heated environment to minimize condensation of semi-volatile substances on the interior surfaces thereof.

It is an object of the present invention to provide an apparatus for the successful performance of chemical processes such as the sequencing of proteins or peptides with an extremely small amount of sample.

It is another object of the present invention to provide an apparatus for the performance of chemical processes such as the sequencing of proteins or peptides with the least sample contamination obtainable.

It is a further object of the present invention to provide an improved fully automated apparatus for the performance of chemical processes such as the sequencing of proteins or peptides.

The closure member of the present invention enables the inner end of the first fluid conduit to be simply and accurately adjusted relative to the annular groove in the spinning reaction cell without contaminating the reaction cell in any way. The various conduits extending through the closure member are rigidly fixed and sealed therein, with the only movable seal in the entire apparatus being that at the the periphery of the closure member against the reaction chamber vessel. It is a relatively simple matter to provide an essentially complete moveable seal at this point, as opposed to an effective rotatable or otherwise adjustable seal about one of the fluid conduits. The prior devices known to the applicant have provided for the adjustability of the pick-up conduit relative to the reaction cell by provision of a rotatable seal about the conduit as it passes through a stationary plug in the reaction vessel. Seals of that type are prone to leakage and chemical deterioration, resulting in contamination of the chemistry within the reaction vessel. The corresponding fixed seals of the present invention may be substantially chemically inert and have virtually complete sealing capabilities, eliminating one of the major sources of contamination in the prior devices.

Another source of system contamination in the prior devices is eliminated by the use of the two series vacuum valves disclosed herein to provide both restricted and full vacuum when required. The restricted passages utilized by prior devices to provide a preliminary restricted vacuum to the reaction chamber have been eliminated in favor of a second vacuum valve provided with a restricted passage through its diaphragm to produce a restricted fluid flow in what would otherwise be its closed position. The second vacuum valve is connected in series with the first vacuum valve and positioned on the vacuum pump side of the first valve such that the restricted vacuum may be turned on and off by opening and closing the first vacuum valve. The first vacuum valve thus entirely closes the second vacuum valve off from the reaction chamber, preventing any condensation of semi-volatile liquids therein. This eliminates the carrying over from one cycle to another of the semi-volatile substances which can become trapped within the restricted vacuum passage of prior devices when the restricted vacuum is shut off. This maintains the sample much freer of contamination than is the case in prior devices, enabling a greater number of degradation steps to be successfully accomplished with a smaller amount of sample.

BRIEF DESCRIPTION OF THE DRAWINGS

The above and other objects of the present invention may be more fully understood from the following detailed description taken together with the accompanying drawings wherein similar reference characters refer to similar elements throughout and in which:

FIG. 1 is a perspective view of an apparatus embodying the improvements of the present invention;

FIG. 2 is a plan view of the apparatus shown in FIG. 1;

FIG. 4 is a vertical sectional view of the reaction chamber of the apparatus of FIG. 1;

FIG. 5 is a top plan view of the structure illustrated in FIG. 4;

FIG. 6 is a perspective view of the reaction cell closure member constructed in accordance with the present invention and shown in FIG. 4;

FIG. 7 is a top plan view of the closure member shown in FIG. 6;

FIG. 8 is a vertical sectional view taken along the lines 8—8 of FIG. 7;

DESCRIPTION OF THE PREFERRED EMBODIMENTS

Figure 3:
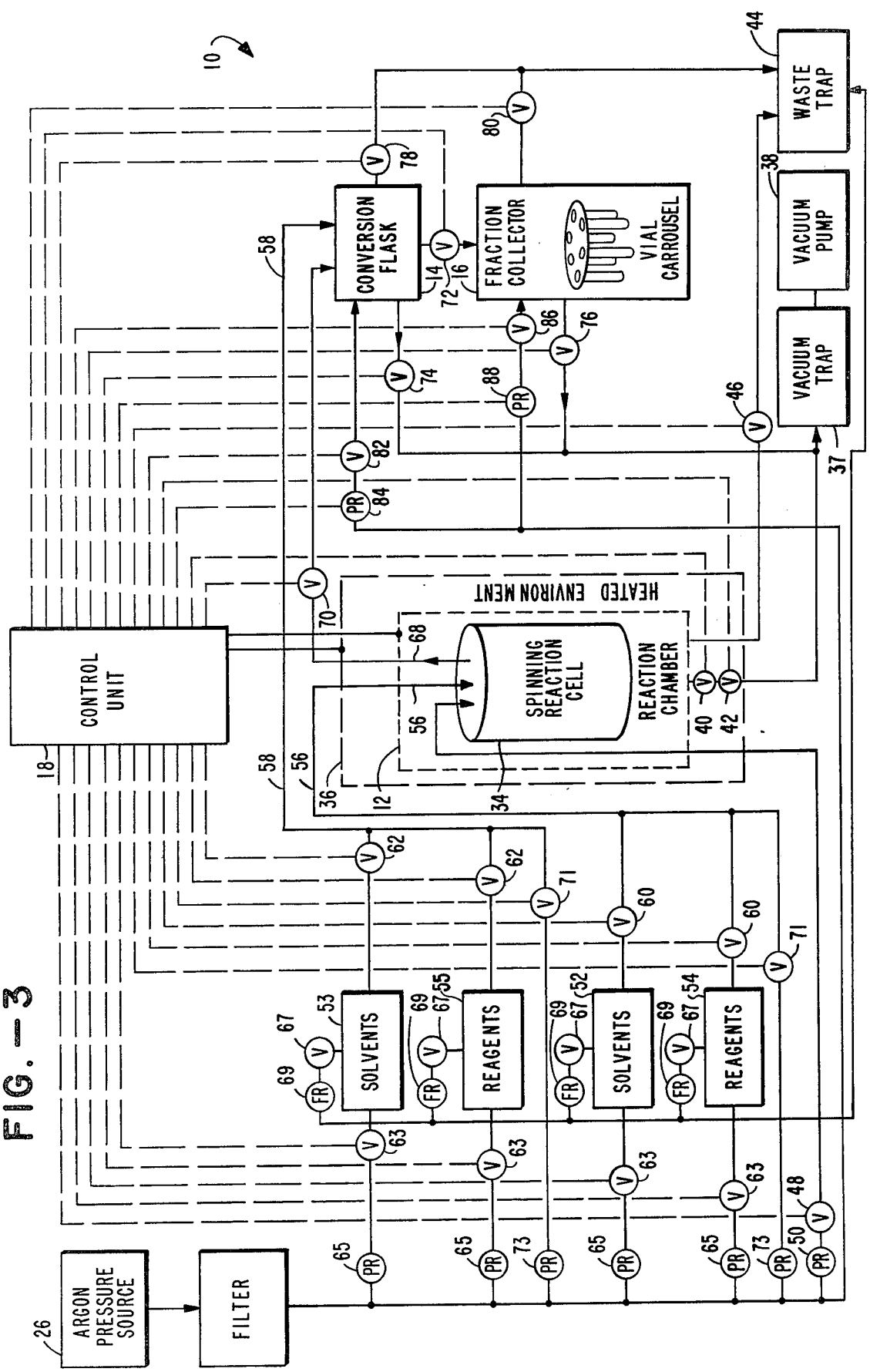
FIG. 3 is a somewhat simplified schematic showing the operation of the apparatus of FIG. 1.

The present invention is primarily an improvement on the prior sequenators described above, particularly the sequenator of Penhasi U.S. Pat. No. 3,725,010 as modified in the articles of Wittmann-Liebold. The technical details of those publications will not be repeated here except as they bear on the improvements disclosed herein. The reader is thus referred to the noted publications for the remaining structural details and the precise timing and sequence of steps involved in the operation of the sequenator.

Referring now to the drawings, there is illustrated, in FIGS. 1 and 2 thereof, an apparatus embodying the present invention, generally designated 10. The apparatus 10 includes a reaction chamber 12, a conversion flask 14 and a fraction collector 16, each of which is operated through an automatic control unit 18. An array 20 of pressurized solvent and reagent reservoirs are connected through a bank 22 of diaphragm type flow valves to the reaction chamber 12 and the conversion flask 14. A second bank of valves 24 regulates the flow of liquids from the reaction chamber to the conversion flask 14 and from the conversion flask to the fraction collector 16, and the flow of gas to and from each of those elements.

Extremely pure argon gas is provided by a filtered argon source 26 for pressurizing the solvent and reagent reservoirs, purging oxygen-bearing air from the system and accelerating the process of drying out the reagents and solvents within the system at various times. A bank 28 of pressure regulating valves and gauges serves to individually regulate the pressure of argon to each solvent and each reagent reservoir, and to each of the other components of the apparatus 12.

The operation of the apparatus 10 is depicted in FIG. 3. The reaction chamber 12 contains a spinning reaction cell 34 and is located within a heated environment 36. The chamber 12 is connectable to a vacuum trap 37 and a vacuum pump 38 by a pair of series connected valves 40 and 42, and to a waste trap 44 through a valve 46. Argon from the source 26 may be introduced into the cell 34 through a valve 48 at a pressure determined by a regulator 50 of the bank 28.

The array 20 includes a plurality of pressurized solvent reservoirs 52 and reagent reservoirs 54 which are individually valved and are manifolded into a conduit 56 which leads to the reaction cell 34, and a plurality of pressurized solvent reservoirs 53 and reagent reservoirs 55 which are individually valved and are manifolded into a conduit 58 which leads to the conversion flask 14. That is, the output of each of the reservoirs 52 and 54 is connected through a different output valve 60 to the manifold of the conduit 56 and the output of each of the reservoirs 53 and 55 is connected through a different output valve 62 to the manifold of the conduit 58. Each of the reservoirs is pressurized with argon gas from the source 26 through a different valve 63 located adjacent the array of reservoirs 20, at a pressure controlled by regulators 65 of the bank 28. The interior of each reservoir is also connected to the waste trap through a vent valve 67 and a flow regulator 69. The flow regulators 69 are simple needle valves or other devices for limiting the flow of gas from the reservoirs when the valves 67 are open. Argon gas may be applied to the manifolds of the conduits 56 and 58 at points upstream of the valves 60 and 62 through a pair of valves 71 having pressure regulators 73 of the bank 28.

When one of the reservoirs is pressurized by the argon source 26 through the appropriate valve 63, flow of the particular solvent or reagent to the cell 34 or the flask 14 may be accomplished by opening the appropriate output valve. The amount of fluid transferred is determined by the length of time the output valve is held open. Each time one of the solvents or reagents is delivered, the delivery is completed by opening the corresponding valve 71 to expel the liquid remaining in the conduit 56 or 58 into the cell 34 or the flask 14. The conduits beyond the valves 60 and 62 are thus purged after each delivery, preventing contamination of the system and the remainder of the apparatus 10 by carrying over solvents and reagents from one step to another.

A conduit 68 having a valve 70 provides a fluid path from the spinning reaction cell 34 to the conversion flask 14. After conversion, valve 72 is opened to pass the fraction from the conversion flask to the fraction collector 16. The conversion flask and the fraction collector may be connected to vacuum by way of valves 74 and 76, respectively, or vented to the waste trap 44 through valves 78 and 80. Argon gas from the source 26 may be introduced into the conversion flask 14 through a valve 82 and a regulator 84, and into the fraction collector 16 through a valve 86 and a regulator 88.

It will be understood that each of the components described above, except the pressure regulators of the bank 28 which include the regulators 84 and 88, is controllable automatically by the unit 18. The regulators are adjusted by hand when the apparatus 10 is initially set up and require no further attention as long as the pressure of the source 26 remains adequate. The valves 46, 48, 60, 62, 70, 71, 72, 74, 76, 78, 80, 82 and 86, comprising all valves in the apparatus 10 which directly communicate with the interior of the chamber 12, the flask 14 or the fraction collector 16, are located in the banks 22 and 24. These valves comprise diaphragm flow valves actuable between open and closed conditions by the alternative application of gas pressure and vacuum to a control port thereof. The application of pressure and vacuum may be controlled by three-way solenoid valves (not shown) actuable for this purpose by the control unit 18. It should be noted that the gas pressure and vacuum for this purpose emanate from sources other than the source 26 and the pump 38 described above, which sources are omitted from the drawings for the sake of simplicity.

The details of the reaction chamber 12 and the surrounding structures are shown in FIGS. 4 and 5. The reaction cell 34 is mounted to an insert 90 adjustably received on a table 92 which is mounted for rotation relative to a bearing housing 94. The bearing housing 94 is received within a cavity 96 in a two-piece base or housing 98 and secured against movement therein by a collar 100 fastened to the lower portion of the housing. A shaft 101 carried by the table 92 extends downwardly through the bearing housing 94 to an annular magnetic element 102. The magnetic element 102 rotates with the table 92 in a recess 104 which is surrounded by a second annular magnetic element 106 mounted for rotation with the drive shaft 108 of a motor 110. The magnetic elements 102 and 106 thus form a magnetic coupling for driving the table 92 and thus the cell 34 by the motor 110. The insert 90 is supported and held on the table 92 by a plurality of set screws (not shown), enabling the position of the cell 34 to be adjusted translationally and angularly within certain limits to achieve precise axial alignment of the cell 34. It should be noted here that the assembly consisting of the reaction cell 34, table 92, bearing housing 94, shaft 101 and magnetic element 102 is substantially the same as that described in Penhasi U.S. Pat. No. 3,725,010, and sold by the assignor thereof, Beckman Instruments, Inc.

A glass column 109 having flanges 111 at its upper and lower ends is positioned generally concentrically about the reaction cell 34 on the stationary housing 98. The upper end of the glass column 109 is covered by a closure member 112 having an enlarged flange portion 114 abutting the upper flange 111 of the column 109 in sealing relationship therewith. The closure member 112 and the column 109 are held against the housing 98 by an upper plate 116 supported by column stud elements 118 threaded into the base 98. The upper plate 116 is fastened to the stud elements 118 by wing nuts 120.

The flat upper and lower surfaces of the flanges 111 of the glass column 109 are finely ground and sealed against the closure member 112 and the housing 98, respectively, by o-rings 122 partially received within those elements. The o-rings 122 provide very effective and trouble-free seals between the various elements.

The detailed structure of the closure member 112 is shown most clearly in FIGS. 6 through 8. Concentric cylindrical portions 124 and 126 are provided on the upper and lower sides of the enlarged flange portion 114, and a smaller cylindrical portion 128 depends eccentrically from the lower cylindrical portion 126 into the interior of the reaction cell 34.

Threaded connector bores 130, 132 and 134 extend generally downwardly from the upper surface of the cylindrical portion 124 for reception of annular connector fittings 136. The inner end of each of the connector fittings 136 and the inner end of the various connector bores are each tapered to seal against the respective sides of doubled-ended ferrules 138. Ferrules 138 seal against the exterior surfaces of respective conduits 140 to provide a complete seal between the exteriors of the conduits and the closure member 112. The ferrules 138 and the conduits 140 are preferably made of a flexible and somewhat resilient material which is substantially chemically inert, such as commercial fluorocarbon polymers. The connections made in this way are fixed and the seals are virtually complete and non-degradable, yielding a structure which is inexpensive to manufacture and yet not susceptible to failure from deterioration or continued use.

A passage 142 extending downwardly from the connector bore 130 communicates with the reaction cell 34, and thus with the chamber 12, for the introduction of argon gas into the chamber as described in relation to FIG. 3. Similarly, a passage 146 connects the bore 134 to a somewhat enlarged passage 148 extending downwardly within the portion 128 for delivery of solvents and reagents to the lower portion of the reaction cell 34. A rigid tube 150 is received within the passage 148 and extends downwardly therefrom. The conduits 140 of the bores 130 and 134 are fed by the valve 48 and the conduit 56, respectively, of FIG. 3.

A passage 152 communicates with the connector bore 132 and extends downwardly through both the cylindrical portion 126 and the eccentric cylindrical portion 128. At a point within the eccentric cylindrical portion 128, the passage 152 opens up to form an enlarged open groove 154 in the side of the portion 128. A segment of rigid tubing 156 forming an elbow extends upwardly into the passage 152 and is retained therein by a set screw 158 such that the exposed end 160 of the elbow 156 extends generally horizontally a short distance from the closure member 112. The conduit 140 which passes through the connector bore 132 is closely received within the rigid elbow 156 and is provided with a lower end 162 extending beyond the elbow end 160 and located at a point displaced from the axis of the closure member 112. The rigid elbow 156 is oriented such that the end 162 is directed generally away from the axis of the closure member and forms an acute angle with the radius of the reaction cell 34 when the apparatus is assembled.

As seen most clearly in FIG. 5, the upper cylindrical portion 124 of the closure member 112 is received for rotation within an eccentric opening 164 in the upper plate 116. In the assembled condition, the lower end 162 of the conduit 140 is located generally opposite a groove 166 adjacent the upper end of the reaction cell 34. Due to the eccentric mounting of the closure 112 and the fact that the lower end 162 of the conduit 140 is displaced from the axis of the closure member 112, rotation of the closure member 112 relative to the remainder of the apparatus 10 causes the lower end 162 to move toward and away from the groove 166 for adjustment thereof. Rotation of the closure member 112 is facilitated by a radially directed handle 168 extending from the enlarged flange portion 114 of the closure member. Fine adjustment of the position of the lower or inner end 162 relative to the groove 166 is thus possible with the apparatus in a fully assembled condition by movement of the handle 168. Optimally, adjustment should be made so that the lower end 162 is within the groove 166 and the conduit 140 adjacent thereto forms an acute angle with the axis of the reaction cell in a manner causing the end 162 to effectively scoop or draw any liquid from the groove 166 as the reaction cell 34 spins about its axis. The withdrawal of fluid from the groove 166 by the lower end 162 is similar to that achieved in the prior devices, however, the method of adjustment to attain this result is entirely different. In the apparatus 10, the only seal which is moved or in any way disturbed by adjustment of the position of the lower end 162 is the upper o-ring 122. Each conduit communicating with the interior of the reaction chamber 12 is fixedly anchored into the closure member 112 and remains stationary relative thereto during adjustment. The structure eliminates all moveable seals of the conduits through the closure member 112, and in so doing eliminates a major source of leakage and contamination. Movement of the large upper o-ring 122 relative to the flat, ground glass surface of the flange 111 does not pose a leakage problem of the type associated with the moveable tubing seals of the prior devices, and the o-ring is not damaged by such movement.

The rigid tube 150 extends downwardly to a point adjacent the bottom of the cell 34 and is displaced slightly from the center of the cell. Fluids introduced into the reaction cell 34 through the tube 150 thus impinge upon the side of the conical projection 170 to facilitate uniform dispersion of such fluids toward the walls of the reaction cell.

The passages through which the vacuum pump 38 is placed in communication with the reaction chamber 12 are shown most clearly in FIG. 4. Vacuum through the valves 40 and 42 of FIG. 3 is applied through the passage 172 in the base or housing 98. The passage 172 communicates directly with the cavity 96 containing the bearing housing 94 and communicates with the upper portion of the chamber 12 adjacent the table 92 and the reaction cell 34 by way of the vertical passage 174. Any gases or vapors within the chamber 12 are thus drawn out the passages 174 and 172 when vacuum is applied. It will be noted here that the chamber 12 comprises not only the space adjacent to and within the reaction cell but also the portions of the cavity 96 surrounding the table 92, bearing housing 94 and magnetic element 102.

Figure 9:
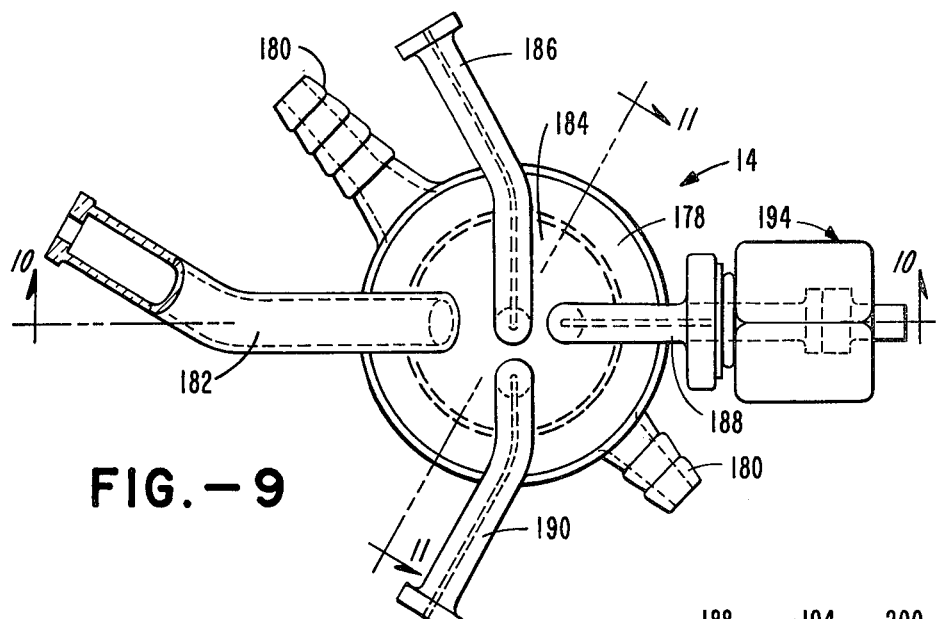
FIG. 9 is a top plan view of a conversion flask constructed in accordance with the present invention.
Figure 10:
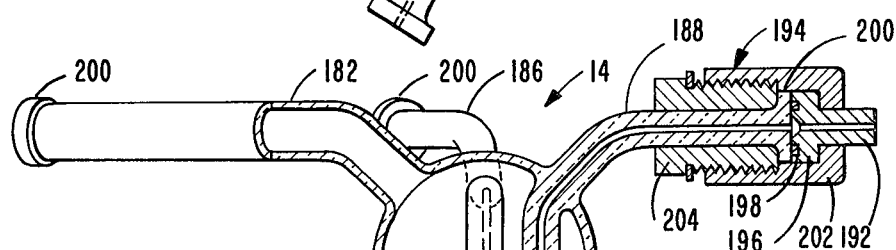
FIG. 10 is a vertical sectional view taken along the lines 10—10 of FIG. 9.
Figure 11:
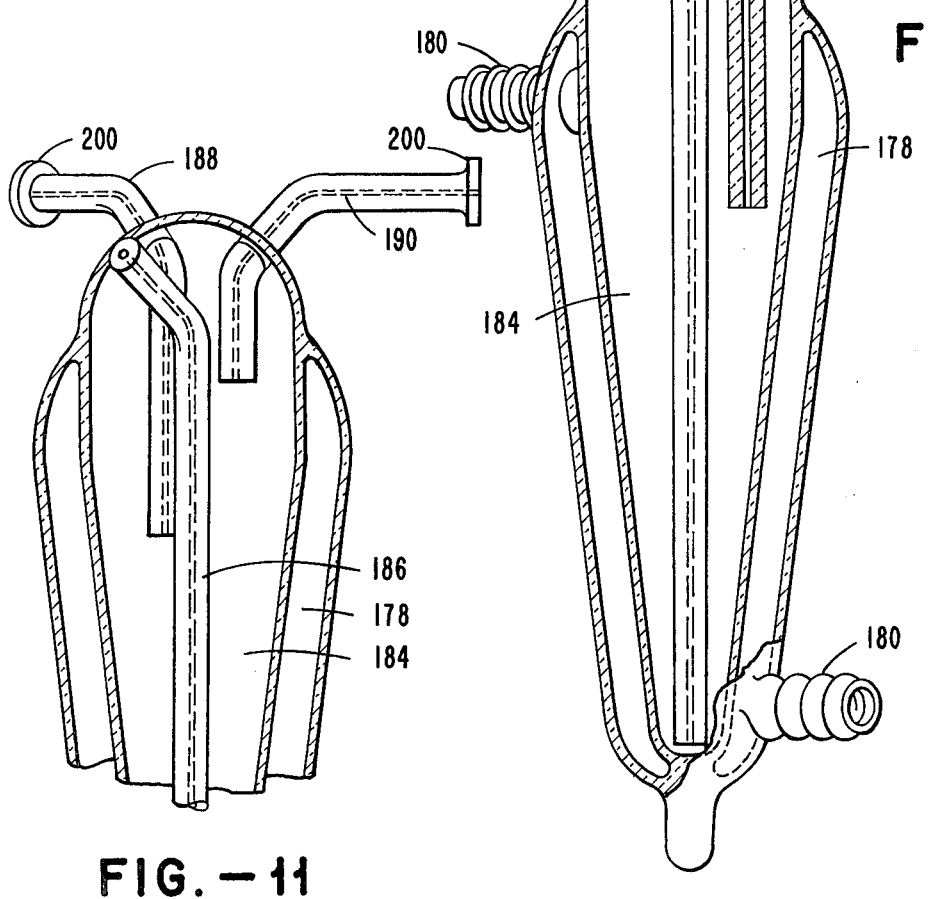
FIG. 11 is a vertical sectional view taken along the lines 11—11 of FIG. 9.

The conversion flask 14 is shown in detail in FIGS. 9 through 11. The flask 14 is of the double-walled glass type having a space 178 between the walls for circulation of a heating fluid such as water. The heating fluid is passed to and from space 178 through a pair of nipples 180 adapted to receive standard flexible tubing ends. A large bore tube 182, connectible to the vacuum trap 37 and the vacuum pump 38 through the valve 74 and to the waste trap 44 through the valve 78, communicates with the interior chamber 184 of the flask adjacent its upper end. Capillary tubes 186, 188 and 180 extend through the upper end of the flask to points within the interior chamber 184. The fractions picked up from the groove 166 of the cell 34 by the lower tubing end 162 are passed sequentially to the flask 14 through the capillary 188. Reagents and solvents enter the interior chamber of the flask through the capillary 190 with sufficient pressure to wash down the surfaces of chamber 184. When the conversion reaction is complete, the fraction is passed upwardly through the long capillary 186 from the narrow base of interior chamber 184 to the respective vial in the fraction collector 16. The use of all glass capillaries 186, 188 and 190 eliminates the problems and chemical contamination associated with the flexible capillaries of the prior devices which are received within and guided by larger bore glass tubing. The two interfitting tubings of the prior devices produce dead air spaces in which semi-volatile solvents and reagents can condense and become trapped. Evacuation of condensation in these areas is generally not possible, leading to contamination of further chemical steps and an eventual reduction in yield.

The outer ends of the tubes 182, 186, 188 and 190 are sealed to respective flexible conduits 192 leading to the various other elements of the apparatus 10 by interfitting screw thread connectors 194. The end of each conduit 192 is provided with a radial flange portion 196 having a resilient o-ring 198 which abuts and seals against the flat ground glass face of a radial flange 200 on one of the glass tubes. An internally threaded collar 202 is slidably positioned over the conduit 192 to receive the glass flange 200 and engage a two-piece externally threaded fitting 204 which is placed about the glass tube. Advancement of the collar 202 over the fitting 204 forces the flange portion 196 against the glass flange 200 to produce an extremely effective seal. The various portions of the connectors 194 may be made of substantially chemically inert materials, such as commercial fluorocarbon polymers, to virtually eliminate the possibility of deterioration and subsequent leakage. The connectors 194 represent a substantial advance over the conversion flask connections disclosed in the papers of Wittman-Liebold. The flask of Wittman-Liebold is provided with glass threads on the exposed ends of the flask tubing for engagement with threaded tubing connectors. These connections pose serious problems of glass breakage when the connectors are tightened, and have been found to permit excessive gas leakage under vacuum. The connectors 194 solve these problems by providing a pair of flat abutting flanges sealed by an o-ring and clamped together by a nonglass screw thread mechanism able to withstand relatively high tightening torques.

An alternative construction of the flask 14 would eliminate the space 178 and the nipples 180, yielding a single-walled vessel which could be maintained at an elevated temperature by placement in the heated environment 36. This structure would have the advantage of maintaining the entire length of the glass tubes and the connectors 194 at the elevated temperature, minimizing condensation of semi-volatile fluids therein, but would not enable the flask and the chamber 12 to be maintained at different temperatures.

Figure 12:
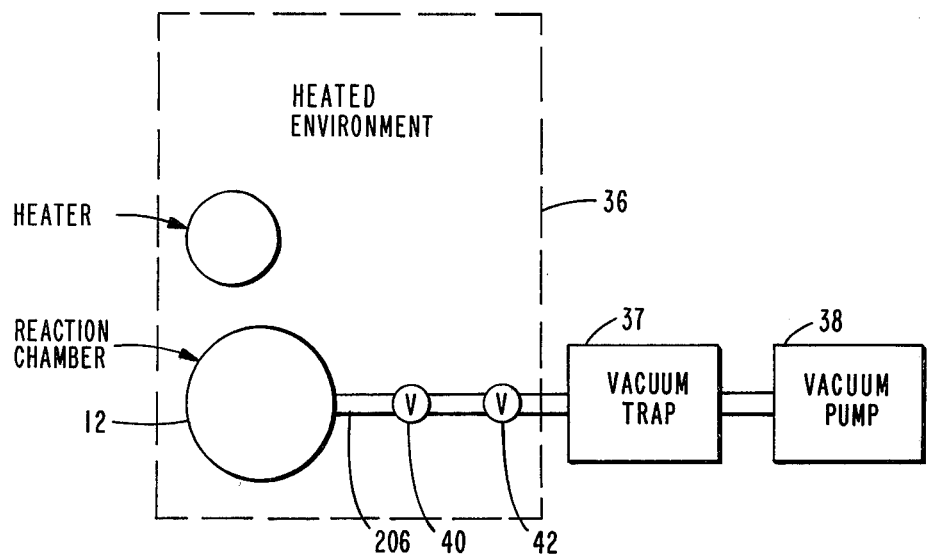
FIG. 12 is a schematic of the vacuum system of the present invention.
Figure 13A:
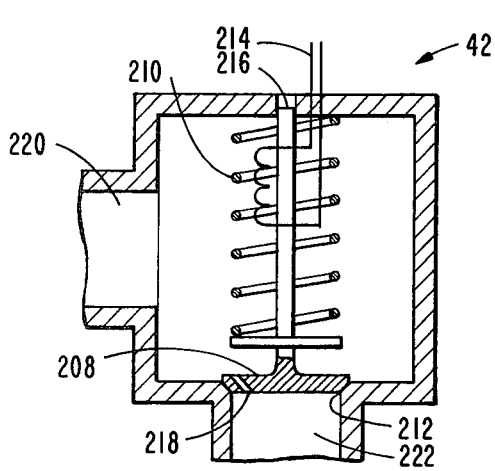
FIG. 13a is a somewhat diagramatic sectional view of the second vacuum valve illustrated in FIG. 12, shown in the restricted condition.
Figure 13B:
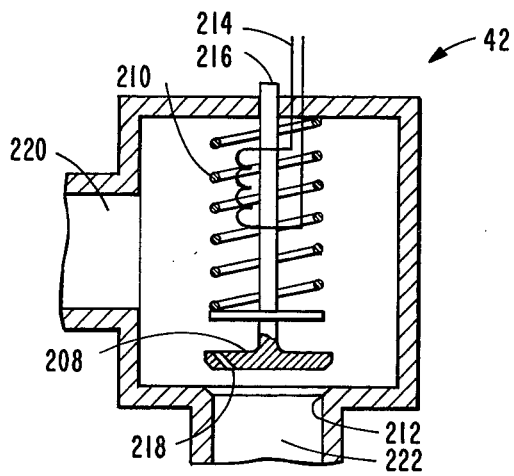
FIG. 13b illustrates the valve of FIG. 13a in the fully open condition.

Turning now to FIG. 12, it is seen that the vacuum source 38 is connectible to the chamber 12 through the vacuum trap 37 and a relatively wide bore conduit 206. The vacuum trap 37 is a stainless steel condenser cooled by liquid nitrogen to trap gases drawn along the conduit 206 by the vacuum pump 38. The application of vacuum to the chamber is controlled by a pair of series-connected solenoid operated valves 40 and 42 which are located within the heated environment or oven 36 along with the chamber 12 and the portion of the conduit 206 between the valves and the chamber. Placement of these elements within the oven 36 greatly reduces problems of condensation within the system. The valve 40 may be a conventional valve actuable between a fully open and a fully closed condition, while the valve 42 is constructed to operate as shown in FIGS. 13a and 13b. A diaphragm or other sealing member 208 is biased by an axial spring 210 to cover a main orifice 212 of the valve body in a peripherally sealing relationship. The diaphragm 208 is actuable by a solenoid apparatus 214 through a connecting rod 216 from the condition of FIG. 13a to that of FIG. 13b. The solenoid apparatus 214 thus operates against the force of the spring 210 such that when the solenoid 214 is deactivated, the diaphragm is returned by the spring 210 to the position shown in FIG. 13a. The diaphragm 208 is provided with a restrictive passage 218 such that in the condition of FIG. 13a a restricted vacuum may be drawn through the valve 42. FIG. 13a thus shows the valve 42 in what is described best as a "restricted open" condition, as opposed to the "fully open" condition of FIG. 13b. The inlet port 220 of the valve 42 is placed in communication with the valve 40 and the outlet port 222 is placed in communication with the vacuum trap 37 and the vacuum source 38.

Full vacuum is applied to the chamber 12 when the valves 40 and 42 are both in the fully open condition, and a restricted vacuum is applied when the valve 40 is in the fully open condition and the valve 42 is in its restricted open condition. No vacuum is applied when the valve 40 is in its fully closed position. This configuration enables either a restricted or full vacuum to be applied to the chamber 12, as desired, without the need for a restricted passage communicating directly with the chamber 12. The problems in the prior art devices of semi-volatile solvents and reagents condensing within a restricted vacuum line are therefore virtually eliminated.

In operation, when a quantity of a particular solvent or reagent is required a dynamic equilibrium is set up within the appropriate reservoir by simultaneously venting the reservoir through the particular valve 67 and applying argon gas at a predetermined pressure through the particular valve 63. This procedure is discussed in detail in Penhasi U.S. Pat. No. 3,725,010, and yields a solvent and reagent delivery system in which the liquids within the output lines are maintained at an essentially constant pressure during delivery. The pressure of the argon introduced to the solvent and reagent reservoirs is determined by the manual setting of the pressure regulators of the bank 28. The solvent and reagent reservoirs 52, 53, 54 and 55 are, of course, each representative of a plurality of such reservoirs, the number of which corresponds to the number of solvents and reagents utilized in the particular sequencing process.

The heated environment 36 is maintained at a constant temperature by the control unit 18 through circulation of thermostatically controlled air therein. The reaction cell 34 is initially caused to spin and is kept spinning throughout the sequencing operation by the variable speed motor 110 under the control of the unit 18. With the upper plate 116 and the closure member 112 removed from the top of the chamber, the sample of the protein or peptide to be sequenced is deposited directly into the reaction cell as it spins to assure formation of a suitable film on the inside wall of the reaction cell. The closure member 112 and the upper plate 116 are then repositioned as shown in FIG. 4 to close the reaction chamber 12, and the reaction chamber is evacuated by opening the valves 40 and 42 to the vacuum trap 37 and the vacuum pump 38.

Each time the reaction cell 12 is evacuated during the sequencing operation, vacuum may be applied to the chamber in a two-step process. Initially, the solenoid valve 40 is actuated and the valve 42 is left at rest such that the valve 40 is fully open and the valve 42 is in its restricted open condition. This applies a restricted vacuum to the reaction chamber 12, evacuating the bulk of the gaseous material therein without subjecting the liquids in the reaction cell 34 to a sudden application of full vacuum which could cause them to boil and thus disrupt the desired pattern of material within the reaction cell. After application of restricted vacuum to the reaction chamber for a predetermined period of time, total vacuum may be applied to the reaction chamber by actuating the valve 42 as well. When the evacuation is to be terminated, the valves 40 and 42 are both allowed to close. The evacuation of the chamber 12 not only removes the elements of air introduced into the chamber when the sample is inserted, but also serves to evacuate the volatile or semi-volatile carrier for the sample. Argon gas from the source 26 may then be introduced into the chamber 12 through the valve 48 to provide an inert atmosphere for carrying on the coupling and cleavage reactions.

Each of the plurality of solvents 52 and reagents 54 is introduced into the spinning reaction cell 34 through the conduit 56 at the appropriate time and in the appropriate amount by the control unit 18. Each time one of the solvents or reagents is required, the procedure noted above for the establishment of a dynamic equilibrium within the particular reservoir is performed. This establishes a predetermined pressure within the particular solvent or reagent line, and flow through the conduit 56 is commenced by opening the appropriate diaphragm valve in the bank 22, represented in FIG. 3 by the valves 60. The amount of the particular reagent or solvent transferred to the reaction cell is established by the length of time that the valve is held open, due to the constant pressure maintained within the particular fluid reservoir. Each time a reagent or solvent is introduced into the conduit 56, the valve 71 is opened to purge the conduit 56 of any remaining liquid, as described above.

During the coupling and cleavage reactions, it is desirable at various times to dry out the sample by evacuating the chamber 12 or passing pressurized argon gas through the chamber. These steps are also accomplished by the control unit 18.

Upon completion of the initial coupling and cleavage reaction, a suitable solvent is introduced into the cell 34 for dissolving the fraction containing the amino acids cleaved from the sample and the speed at which the cell 34 spins is increased automatically. In this way, the fraction is forced up the interior wall of the cell 34 into the annular groove 166 shown in FIG. 4. The valve 70 is then opened to allow the fraction to be scooped or drawn from the groove 166 by the lower conduit end 162 depending from the closure member 112, and transferred to the conversion flask 14. Upon completion of the transfer, these steps may be repeated one or more times with the introduction of additional solvent into the cell 34 for thoroughly washing the first fraction from the sample. The sample in the cell 34 is left as a film on the interior surface of the cell 34 and is ready for the next coupling and cleavage steps.

The fraction transferred to the conversion flask 14 may be converted automatically during the next coupling and cleavage cycles of the cell 34, according to the articles noted above by Wittman-Liebold. Briefly, the amino acid fraction within the conversion flask may first be evaporated by the passage of argon gas over the solution through the short capillary 190 and bubbling of argon gas up through the liquid by way of the capillary 186, followed by application of vacuum through the tube 182. The conversion reagent may then be introduced through the capillary 190 by way of the conduit 58 and one of the valves 62 of the valve bank 22 in the desired quantity. Evaporation of the conversion reagent may be commenced during the latter portion of the conversion reaction period by the argon drying process noted above to avoid excessive reaction times. The final evaporation of the conversion reagent may be accomplished by applying vacuum to the conversion flask through the tube 182. The amino acid remaining within the conversion flask is then redissolved in an appropriate solvent introduced through the conduit 58 for transfer of the fraction to the appropriate vial in the fraction collector 16. The transfer of the fraction is accomplished by opening the valve 72 connected to the long central capillary 186 of the conversion flask and admitting pressurized argon gas through the capillary 190 to force the fraction from the flask.

The argon drying process described above in relation to the various components of the apparatus 10 may be accomplished either by venting the particular component to the waste trap 44 as argon is introduced or by connecting the component to vacuum as argon is introduced.

The apparatus 10 is fully automated such that the predetermined sequence of events is performed by the unit 18 without human intervention once it is initially set up. After inserting the sample within the reaction cell and closing the chamber 12, the apparatus 10 is operable to couple, cleave and convert the various amino acid units of the sample into the same number of fractions in the carousel of the fraction collector 16. While the precise sequence and duration of steps is dependent on the sample and reagents used, the apparatus 10 is operable according to the sequence of steps set out in the Penhasi U.S. Pat. No. 3,725,010, as modified in the Whittman-Liebold articles to include the automated conversion steps.

In the alternative, the structure of the present invention relative to the reaction chamber 12 and the series-connected vacuum valves 40 and 42 may be incorporated directly into the apparatus of the Penhasi U.S. Pat. No. 3,725,010, yielding a system which lacks the conversion flask 14 and passes the products of the cleavage reaction steps directly to the fraction collector 16 from the cell 34. The sequence of steps, the plumbing and the control mechanism of Penhasi U.S. Pat. No. 3,725,010, as modified in the above-noted papers of Hunkapiller and Wittman-Liebold, would then be applicable to this system.

A further possibility for use of the novel structures of the present invention is a device for the manual performance of chemical processes. The processing steps would then be executed by manual operation of each valve and mechanical device in a sequence determined by the operator. One example of a sequence of steps useful in such a case is that of the Penhasi patent.

The various components of the apparatus 10 are preferably constructed of materials which are substantially inert and are highly resistant to deterioration. Such materials include borosilicate glass, certain fluorocarbon polymers, and, in some cases, stainless steel and aluminum. The sealing structures and other elements of the apparatus 10 have been designed such that they can be manufactured almost exclusively from these materials. It is felt that the resulting apparatus is the cleanest and most contamination free system obtainable and will function in that condition indefinately.

From the above, it can be seen that there has been provided an improved apparatus for automatically performing chemical processes which considerably reduces contamination in successive cycles of operation and thereby produces a greatly increased yield from a substantially smaller sample.

The appended claims are intended to cover all variations and adaptations falling within the true scope and spirit of the present invention.

We claim:

1. An improved apparatus for the performance of chemical processes of the type including a base, a vessel on said base at least partially defining a reaction chamber having an open end, a reaction cell mounted within the chamber and having a substantially cylindrical axially directed interior wall in which is formed an annular groove, and means for spinning the cell about its axis to distribute a chemical compound on said interior wall as a thin film, wherein the improvement comprises:

a closure member mounted for rotation between a plurality of positions relative to the base about an axis displaced a first predetermined distance from the axis of the cell, said closure member sealingly engaging the open end of the chamber for each of said positions; and a first fluid conduit extending through the closure member and terminating at an inner end within the cell for the withdrawal of fluid therefrom, said inner end being displaced a second predetermined distance from the axis of rotation of the closure member at a location substantially opposite the annular groove;

such that the inner end of said first conduit is actuable for purposes of adjustment between a first location displaced radially from the annular groove and a second location substantially within the groove by rotation of the closure member through a preselected angle, the first conduit being operable to receive fluid from the groove for the inner end at said second location.

2. The processing apparatus recited in claim 1 which includes a second fluid conduit carried by said closure member and terminating at an inner end within said cell for the introduction of fluids into the cell, said second conduit actuable between second and third locations spaced from the axis of the cell by rotation of the closure member through a preselected angle.

3. The processing apparatus recited in claim 1 wherein the inner end of said first conduit is directed generally away from the axis of rotation of the closure member and forms an acute angle with a radius of the reaction cell.

4. The processing apparatus recited in claim 1 wherein said first conduit is a flexible tube received within a curved rigid conduit adjacent the underside of the closure member for directing the inner end of the flexible tube generally away from the axis of rotation of the closure member to form an acute angle with a radius of the reaction cell.

5. The processing apparatus recited in claim 1 which includes means for fixedly anchoring said first and second conduits into said closure member in sealing relationship.

6. The processing apparatus recited in claim 5 wherein said anchoring means comprise resilient ferrules engaged with the exterior of said first and second conduits in a force kit relationship and compressed by screw thread means to form a stationary seal between the exterior of said conduits and said closure member.

7. The processing apparatus recited in claim 6 wherein said resilient ferrules are made of a material which is substantially chemically inert.

8. The processing apparatus recited in claim 1 wherein said closure member is provided with lever means to facilitate rotation thereof between said plurality of positions.

9. An improved apparatus for the performance of chemical processes of the type including a base, a vessel on said base at least partially defining a reaction chamber having an open upper end, an upright reaction cell mounted within the chamber and having a substantially cylindrical axially directed interior wall in which is formed an annular groove, and means for spinning the cell about its axis to form a thin chemically reactive film on said interior wall, wherein the improvement comprises:

a closure member mounted for rotation between a plurality of positions relative to the base about an axis displaced a first predetermined distance from the axis of the cell, said closure member sealingly engaging the open end of the chamber for each of said positions; and a first fluid conduit extending through the closure member and terminating at an inner end within the cell for the withdrawal of fluid therefrom, said inner end being displaced a second predetermined distance from the axis of rotation of the closure member at substantially the height of the annular groove;

such that the inner end of said first conduit is actuable for purposes of adjustment between a first location displaced radially from the annular groove and a second location substantially within the groove by rotation of the closure member through a preselected angle, the first conduit being operable to receive fluid from the groove for the inner end at said second location.

10. An improved apparatus for the performance of chemical processes of the type including a base, a vessel on said base at least partially defining a reaction chamber, means for closing an open end of the chamber while permitting the introduction and withdrawal of a plurality of fluids relative to the chamber and a vacuum source connectible to the chamber, wherein the improvement comprises:

first valve means between the vacuum source and the chamber, said first valve means actuable between a fully open and a fully closed condition; and second valve means in series with the first valve means, said second valve means actuable between a fully open condition and a restricted open condition;

whereby full vacuum is applied to the chamber when both valve means are in the fully open condition, a restricted vacuum is applied when the first valve means is in the fully open condition and the second valve means is in the restricted open condition, and no vacuum is applied when the first valve means is in the fully closed condition.

11. The processing apparatus recited in claim 10 wherein said second valve means is provided with a valve element which moves in and out of position to close off a fluid conduit, said valve element having a restricted passage therethrough to provide a restricted fluid flow when the valve element is in position to close off the fluid conduit.

12. The processing apparatus recited in claim 10 wherein said second valve means is located in the fluid path from said first valve means to the vacuum source.

13. The processing apparatus recited in claim 10 wherein said first and second valves and the lines connecting said valves to each other and to the chamber are located within a heated environment to minimize condensation of semi-volatile fluids on the interior surfaces thereof.

14. An improved apparatus for the automated performance of chemical processes of the type including a base, a vessel on said base at least partially defining a reaction chamber having an open end, a reaction cell mounted within the chamber and having a substantially cylindrical axially directed interior wall in which is formed an annular groove, means for spinning the cell about its axis to form a thin chemically reactive film on said interior wall, means for introducing and withdrawing a plurality of fluids relative to the interior of the chamber and the cup, and means for automatically controlling said spinning means and said introduction and withdrawal means, wherein the improvement comprises:

a closure member mounted for rotation between a plurality of positions relative to the base about an axis displaced a first predetermined distance from the axis of the cell, said closure member sealingly engaging the open end of the chamber for each of said positions; and a first fluid conduit extending through the closure member and terminating at an inner end within the cell for the withdrawal of fluid therefrom, said inner end being displaced a second predetermined distance from the axis of rotation of the closure member at a location substantially opposite the annular groove;

such that the inner end of said first conduit is actuable for purposes of adjustment between a first location displaced radially from the annular groove and a second location substantially within the groove by rotation of the closure member through a preselected angle, the first conduit being operable to recieve fluid from the groove for the inner end at said second location.

15. For use in an apparatus for the performance of chemical processes of the type including a base, a vessel on said base at least partially defining a reaction chamber having an open end, a reaction cell mounted within the chamber and having a substantially cylindrical axially directed interior wall in which is formed an annular groove, and means for spinning the cell about its axis to distribute a chemical compound on said interior wall as a thin film, a closure structure which comprises:

a closure member mountable for rotation between a plurality of positions relative to the base about an axis displaced a first predetermined distance from the axis of the cell, said closure member sealingly engageable with the open end of the chamber for each of said positions; and a first fluid conduit extending through the closure member and terminating at an inner end within the cell when the closure member is mounted for rotation relative to the base, said inner end being displaced a second predetermined distance from the axis of rotation of the closure member at a location substantially opposite the annular groove;

such that the inner end of said first conduit is actuable for purposes of adjustment between a first location displaced radially from the annular groove and a second location substantially within the groove by rotation of the closure member through a preselected angle, the first conduit being operable to receive fluid from the groove for the inner end at said second location.

16. An improved apparatus for the performance of chemical processes of the type including a base, a vessel on said base at least partially defining a reaction chamber having an open end, a reaction cell mounted within the chamber and having a substantially cylindrical axially directed interior wall in which is formed an annular groove, and means for spinning the cell about its axis to distribute a chemical compound on said interior wall as a thin film, wherein the improvement comprises:

a conversion flask having a plurality of glass capillaries extending into the interior thereof;

means for connecting said capillaries to the interior of said cell and other locations within the apparatus for the selective transfer of fluids to and from said flask;

whereby fluids can be transferred through said capillaries between said flask and said cell and between said flask and said other locations for performance of various chemical processes.

17. The processing apparatus recited in claim 16 wherein said connecting means comprises:

a radial glass flange carried at the end of each of said capillaries outside the flask and having a substantially flat outer face;

radial flange means carried at the ends of a plurality of flexible conduits leading to the interior of the cell and said other locations, each of the outer faces of said flange means having a substantially flat sealing face provided with an annular resilient sealing member received therein for sealing against one of said glass flanges when said outer faces are caused to abut each other;

means for clamping said glass flanges against said flange means such that said outer faces abut said sealing faces to provide a sealed connection between said capillaries and said flexible conduits.

* * * * *